United States Patent [19]

Mill et al.

[11] 4,003,792

[45] Jan. 18, 1977

[54] CONJUGATES OF ACID POLYSACCHARIDES AND COMPLEX ORGANIC SUBSTANCES

[75] Inventors: Patrick James Mill, Beaconfield; Michael Alan Cresswell, High Wycombe; Joseph George Feinberg, London, all of England

[73] Assignee: Miles Laboratories, Inc., Elkhart, Ind.

[22] Filed: Aug. 8, 1972

[21] Appl. No.: 278,880

Related U.S. Application Data

[63] Continuation of Ser. No. 741,212, June 28, 1968, abandoned.

[30] Foreign Application Priority Data

July 1, 1967 United Kingdom ............ 31374/67

[52] U.S. Cl. ............................ 195/63; 260/112 R; 260/112.7; 260/121; 260/209.5; 260/209.6; 424/12; 424/89; 424/91; 424/92; 195/68; 195/DIG. 11; 536/2; 536/3

[51] Int. Cl.$^2$ .................. C07G 7/00; C07C 103/52

[58] Field of Search .................. 424/12, 89, 91, 92; 260/112 R, 209.5, 209.6, 112.7, 112 B, 121; 195/63, 68, DIG. 11

[56] References Cited

FOREIGN PATENTS OR APPLICATIONS 1,174,854   12/1969   United Kingdom

OTHER PUBLICATIONS

Chemical Abstracts, vol. 61, entry 9706c, 1964, citing Micheel et al., Makromol. Chem., vol. 48, pp. 39-49, 1961.

Primary Examiner—Lewis Gotts
Assistant Examiner—Reginald J. Suyat
Attorney, Agent, or Firm—Myron B. Sokolowski

[57] ABSTRACT

This invention relates to chemical conjugates of acid polysaccharides and biochemically active complex organic molecules and particularly to such conjugates which are capable of forming soluble sodium salts and insoluble calcium salts.

32 Claims, No Drawings

CONJUGATES OF ACID POLYSACCHARIDES AND COMPLEX ORGANIC SUBSTANCES

This is a continuation of application Ser. No. 741,212, filed June 28, 1968, now abandoned.

The present invention provides a conjugate consisting of a complex, biochemically active organic molecule (hereinafter called the active component) covalently linked to a polysaccharide containing acid groups (hereinafter called the acid polysaccharide) via a proportion of the acid groups such that the conjugate, like the polysaccharide, containing free acid groups itself, is capable of forming a water-soluble sodium salt and a water-insoluble calcium salt. Linkage is generally effected through basic amino or phenolic hydroxyl groups of the active component to the acid groups of the polysaccharide. The term "basic amino group" as used herein means any —NH— group capable of forming an addition salt with an acid.

The acid polysaccharides used form water-soluble sodium salts and water-insoluble calcium salts and the conjugation is performed in such a manner that these properties as well as the biochemical activity of the active component are preserved in the final product.

Examples of suitable acid polysaccharides are pectin, pectic acid, alginic acid, celluronic acid, and carrageenan.

Pectin is a natural product isolated e.g. from apples and citrus fruits, and consists of a polymer predominantly of galacturonic acid in which some of the carboxyl groups are esterified. Pectic acid is the free acid obtained by saponification of pectin. Alginic acid is a natural product isolated from algae and consists of a polymer predominantly of mannuronic acid with possibly some glucuronic acid. Celluronic acid is a polymer of glucuronic acid and glucose produced by controlled partial oxidation of cellulose with nitrogen dioxide. For the purposes of this invention, the oxidation product is dissolved in aqueous alkali, neutralized and precipitated as the calcium salt. The calcium is then removed by treatment with ethylenediaminetetraacetic acid disodium salt and dialysis against water to reconstitute the soluble sodium salt of the celluronic acid.

These acid polysaccharides were used either as the sodium salts obtained by freeze-drying their solutions in vacuo, or as the free acids, obtained by treating the dried sodium salts repeatedly with excess ethanolic HCl, washing with ethanol, and drying in vacuo.

Carrageenan is a natural product obtained from certain algae and consists of a sulfated polymer of galactose and anhydrogalactose. Suitable material for conjugation may be obtained by adding a calcium salt to a solution of the carrageenan, collecting the precipitate of calcium salt which forms, dissolving it by the addition of ethylenediaminetetraacetic acid disodium salt and dialyzing the solution against water. The solution obtained is passed through a column of a strong cationic exchange resin in the hydrogen form and the resulting solution of the free acid carrageenan is treated with sufficient sodium hydroxide solution to half neutralize the acid groups, Finally this solution is freeze-dried in vacuo.

The active component of the conjugates may be any complex organic material containing basic amino (as defined herein) or phenolic hydroxyl groups. Generally, these materials are proteinaceous substances such as proteins, polypeptides, peptones and proteoses which materials undergo hydrolysis in the presence of acids or enzymes to yield a mixture of alpha amino acids. Thus, by definition and as used herein, proteinaceous substances are those complex organic materials made up of individual amino acid segments. A second type of active component which will form conjugates with acid polysaccharides are those containing phenolic hydroxyl groups. Examples of the active component of the present invention are extracts of allergenic or antigenic substances, extracts of microorganisms, microbial products, toxins, toxoids, hormones and enzymes. Specific examples of allergens are extracts of pollens, such as from trees and ragweed, extracts of proteins of foods, of fungi, of animal epidermis or dander, of insects and of house dust. The active component may also be a small molecule which is not antigenic in itself but becomes so when part of the large conjugate molecule, i.e. a hapten.

The new conjugates are produced by methods for the covalent bonding of complex organic compounds containing basic amino or phenolic hydroxyl groups to acids and in this regard it is important to choose a technique which will neither destroy the biochemical activity of the components not introduce undesirable groups into the conjugate. These techniques generally utilize a coupling agent.

One method involves the use of a water-soluble diimide such as the metho-p-toluene sulfonate of 1-cyclohexyl-3-morpholinylethylcarbodiimide as the coupling agent. In this method, the acid polysaccharide and the antigen are mixed in aqueous solution with the aforesaid reagent. The latter is converted into the corresponding urea, and the acid groups of the polysaccharide react with the basic amino or phenolic hydroxyl groups of the active component to form amido or ester linkages, respectively. In a second suitable method, the acid polysaccharide is first reacted with ethyl chloroformate in the presence of triethylamine to produce a mixed anhydride, and the latter is then reacted with the active component to form amide or ester linkages between the constituents of the conjugation. In a third method, the acid polysaccharide is reacted with N-hydroxypiperidine in the presence of N,N'-dicyclohexylcarbodiimide to produce the N-hydroxypiperidine ester of the acid polysaccharide. This latter ester is then reacted with the active component which becomes linked to the acid polysaccharide via amide or possibly ester linkages with liberation of N-hydroxypiperidine. In the fourth method, a partially esterified acid polysaccharide is reacted with hydrazine hydrate with formation of the corresponding hydrazide. This hydrazide is then treated with nitrous acid to produce the corresponding azide, and the latter is reacted with the active component which becomes linked to the acid polysaccharide via amide or ester linkages. In a fifth method an amine or metal salt of the polysaccharide is first reacted with sulfur trioxide-N,N'-dimethylformamide complex to produce a mixed anhydride, which is subsequently reacted with the active component with the formation of amide or ester linkages. All these methods have the advantage that they can be carried out in aqueous solution at relatively low temperatures. The application of them to the production of the conjugates in accordance with the present invention is described in the Examples below. However, it should be noted that other coupling agents may be used as well.

Whichever of the aforesaid methods is used, the desired conjugate is in general obtained as an aqueous solution. From this, it is preferably isolated by precipitation as the calcium salt which is filtered off and washed thoroughly with water to remove any unreacted antigen. The washed calcium salt is then dissolved in an aqueous solution of sodium ethylenediaminetetraacetate and sodium carbonate, and the solution obtained is dialyzed. The dialyzed solution is then dried to give the conjugate in the form of its sodium salt.

In order to insure that the conjugate contains free acid groups, it is in general desirable to use an excess of the acid polysaccharide so that the final conjugate contains free acid groups and is capable of forming a water-soluble sodium salt and insoluble calcium salt. The proportion of protein introduced into a conjugate may be determined by methods of protein analysis such as the Kjeldahl nitrogen estimation.

The conjugates of the present invention have been found useful in reagent systems employing a soluble form of a biochemically active substance which can be or is insolubilized, in situ, the conjugate retaining its activity throughout the process. Alternatively, the insoluble form of the conjugate can be prepared and used as such. An example of in situ insolubilization involves use of a soluble conjugated enzyme or other proteinaceous substance such as albumin to clarify fruit juices and then removing the conjugate by the addition of calcium ion. Another use resides in employing an insoluble antigen conjugate to effect a slow release of antigen in tissue. Such slow release in tissue is often called a depot effect. The present conjugates can also be used for the preparation of antisera in animals to toxins, e.g., snake Naja Naja (Cobra venom).

In the dry state, the new conjugates have good storage stability.

The following Examples illustrate the invention.

EXAMPLE 1

Alginic acid (10 g., 0.046 equivalents) and 1-cyclohexyl-3-morpholinylethyl-carbodiimide metho-p-toluene sulfonate (10 g., 0.024 mole) were stirred with triethylamine (3.05 ml., 0.022 mole) and the sodium salt of ovalbumin (1 g.) in water (200 ml.) for seven days. After this time, calcium acetate solution (10%, 100 ml.) was added, and the resultant precipitated gel was filtered off and washed with distilled water (1 liter) for an hour and then centrifuged. This washing was repeated seven times, using on one occasion 2 liters of water and stirring overnight. The washed gel finally obtained was then dissolved in an aqueous solution of sodium ethylenediaminetetraacetate and sodium carbonate, and the solution obtained was dialyzed against distilled water. The dialyzed solution was freeze-dried, and 9 g. of product was obtained. It was found to have a protein content of 5–6% by kjeldahl analysis and was useful as a slow release antigenic substance for studying antigen-antibody response in mice over a prolonged period of time.

EXAMPLE 2

Pectic acid (10 g., 0.046 equivalents) and 1-cyclohexyl-3-morpholinylethylcarbodiimide metho-p-toluene sulfonate (10 g., 0.024 mole) were stirred with triethylamine (3.05 ml., 0.022 mole) and the sodium salt of ovalbumin (1 g.) in water (200 ml.) for seven days. The resulting solution was then worked up as described in Example 1, and 10 g. of a conjugated product was obtained containing 3–4% of protein. This product was useful as in Example 1.

EXAMPLE 3

Celluronic acid (3 g., 0.005 equivalents), the sodium salt of ovalbumin (0.3 g.), triethylamine (0.33 ml., 0.0024 mole) and 1-cyclohexyl-3-morpholinylethylcarbodiimide metho-p-toluene sulfonate (3 g., 0.0072 mole) were stirred in water (50 ml.) for 1 week. A solution of calcium acetate (10%, 50 ml.) was then added, and the gel obtained was washed free of antigen as described in Example 1. It was then dissolved in an aqueous solution of sodium ethylenediaminetetraacetate and sodium carbonate, dialyzed and freeze-dried as described in Example 1, to give the desired conjugate (1.2 g.), which was found on analysis to have a protein content of 1.8%.

The mother liquor separated after the precipitation of the conjugate as its calcium salt was treated with a further solution of calcium acetate (10%, 20 ml.), and the precipitate produced was separated, washed several times with dilute calcium acetate solution, and then dissolved and dialyzed as already described for the main precipitate. A second crop of the desired conjugate (1.0 g.) was obtained, having a protein content of 2.8%. This conjugate was useful as in Example 1.

EXAMPLE 4

Finely divided alginic acid (2 g.) was stirred with triethylamine (1.32 ml., 0.0095 mole) and ethyl chloroformate (0.44 ml., 0.0046 mole) in dioxane at 5° C. for 1 hour. The product was filtered off and added to a solution of the sodium salt of ovalbumin (100 mg. in 25 ml. of water). After stirring for several days, the conjugate was precipitated by the addition of an excess of calcium acetate solution (10%, 20 ml.), and the precipitate was separated and thoroughly washed with water. After dissolution in an aqueous solution of sodium ethylenediaminetetraacetate and sodium carbonate, and dialysis against water as described in Example 1, followed by freeze-drying, the desired conjugate (1.2 g.) was obtained, and was found on analysis to contain 2.5% of protein. It was useful as in Example 1.

EXAMPLE 5

Alginic acid (1.76 g., 0.008 equivalents) was stirred, in suspension in tetrahydrofuran (50 ml.), with N,N'-dicyclohexylcarbodiimide (1.03 g., 0.005 mole) and N-hydroxypiperidine (1.5 g., 0.015 mole) for 2 days. The product was filtered off and washed with methanol to remove the N,N'-dicyclohexylurea produced. The N-hydroxypiperidine ester of alginic acid was obtained in a yield of 1.9 g. Timothy pollen extract (25 mg.) was dissolved in a little water and the solution brought to a pH of 7–8 by the addition of 0.01 N sodium hydroxide solution. A suspension of the N-hydroxypiperidine ester of alginic acid (500 mg.) in water (20 ml.) and triethylamine (0.15 ml., 0.0011 mole) were then added. The mixture was stirred for three days, and the conjugate then precipitated by acidification to pH 4 with dilute hydrochloric acid. The precipitated conjugate was dissolved in sodium carbonate solution, and the solution then dialyzed against water. Freeze-drying of the dialyzed solution gave the desired conjugate (200 mg.), which was found on analysis to contain 6–7% of protein. It was useful as a depot antigen for effecting prolonged hyposensitization in mammals.

EXAMPLE 6

Pectin hydrazide was produced by refluxing one equivalent of sodium pectinate with two equivalents of hydrazine hydrate in methanol for 2 hours. The hydrazide was filtered off, washed with methanol and dried. An alternative method for producing the hydrazide was to mix one equivalent of sodium pectinate with five equivalents of hydrazine hydrate in methanol, and to allow the mixture to stand for 2 days at room temperature before filtering off, washing and drying the solid. In both cases, the pectin hydrazide product had the same physical form as the original pectin.

Pectin hydrazide sodium salt (1 g.) was dissolved in water (50 ml.) at 0° C., and sodium nitrite (0.117 g., 0.0017 mole) and 1N hydrochloric acid (6 ml., 0.006 mole) were added. During this addition, the pectin was partially precipitated. The reaction was allowed to proceed at 0° C. for 30 minutes. Sufficient sodium bicarbonate solution was then added to dissolve the product and bring the pH of the mixture to 7–8. Freeze-dried Timothy pollen extract (50 mg.) in neutral solution in water (10 ml.) was then added and stirring was continued for 3 days. The product was precipitated by the addition of calcium acetate solution (10%, 10 ml.), and the gel obtained was washed thoroughly with distilled water and separated by centrifugation. The washing and centrifugation were repeated 10 times. The washed gel was then dissolved in an aqueous solution of sodium ethylenediaminetetraacetate and sodium carbonate, and the solution was dialyzed against distilled water and freeze-dried to give the desired conjugate (0.52 g.), which was found on analysis to contain 6.3% of protein. This conjugate was useful as in Example 5.

EXAMPLE 7

Carrageenan (2 g., 0.01 equivalents) was suspended in tetrahydrofuran (50 ml.) at 0° C. and then triethylamine (1.17 ml., 0.0085 mole) and ethyl chloroformate (0.82 ml., 0.086 mole) were added. The mixture was stirred for 2¼ hours and then the mixed anhydride, which had been formed, was collected by filtration and added to a solution of ovalbumin (200 mg.) in water (60 ml.).

After two days at 0° C., the product was precipitated by adding calcium acetate (20 ml. of a 10% solution). It was thoroughly washed with dilute calcium acetate solution (0.01 M) to remove free protein. The gel was then dissolved by adding sodium carbonate, to give a pH of 9–10, and a slight excess of ethylenediaminetetraacetic acid, disodium salt. The solution was dialyzed against water and then dried from the frozen state to give 300 mg. of a product containing 3–4% protein. This product was useful as in Example 1.

EXAMPLE 8

Alginic acid triethylamine salt (0.7 g., 0.0025 equivalents) was suspended in dry dimethylformamide (15 ml.) and cooled to −5° C. Ethyl chloroformate (1 ml., 0.0104 mole) was added and the solution was stirred at 0° to −10° C. until the suspended triethylamine salt dissolved. This solution was added to a previously prepared solution of 200 mg. of cocksfoot pollen extract in 35 ml. of ice-cold water. The pH of the cooled solution was adjusted to 8 and kept constant over the initial period of the reaction. The mixture was then stirred overnight in the cold room before the conjugate was precipitated by the addition of calcium solution (10%, 20 ml.). The product was worked up as described in Example 1 and 450 mg. of conjugate were obtained which on analysis was found to have a protein content of 4%. The conjugate was useful as in Example 5.

EXAMPLE 9

Dry sodium pectate (0.5 g., 0.0025 equivalents) was suspended in 20 ml. of dry dimethylformamide. To this were added 0.4 ml. of dimethylformamide containing 0.0014 mole of sulphur trioxide-dimethylformamide complex. The mixture was allowed to stand at room temperature for 3 weeks and then the pectate complex was collected by filtering and added to a solution of 280 mg. of ragweed pollen extract in ice-cold water. The mixture was stirred for 2 days at 2° C. and then the conjugate was precipitated as its calcium salt and worked up as in the previous examples to give 0.5 g. of product which on analysis had a protein content of 3.5%. The conjugate was useful as in Example 5.

EXAMPLE 10

Alginic acid triethylamine salt (120 mg., 0.0004 equivalents) was suspended in 15 ml. of dry dimethylformamide and cooled to −5° C. Ethyl chloroformate (0.25 ml., 0.0026 mole) was added and stirring was continued at −5° C. for 2 hours. The resulting solution of the mixed anhydride was then poured into tetrahydrofuran (25 ml.) and stirred for a few minutes. The precipitated mixed anhydride was filtered off and added to a solution of diphtheria toxin (1250 Lf.) in 20 ml. of ice-cold water. The pH of the solution was adjusted to 8 and stirring was continued overnight. The conjugate was precipitated as its calcium salt and worked up as described in the previous examples to give 90 mg. of product. The conjugate was found useful in immunizing mammals.

EXAMPLES 11–61

The following table lists conjugates which have been prepared, giving the polysaccharide component, the antigen or protein component, and indicating the coupling method (M.A. = mixed anhydride method using ethyl chloroformate; W.S.D. = water soluble diimide method; $SO_3$ = $SO_3$ - complex anhydride methods; N.H.P. = N = hydroxy piperidine active ester method; A.Chl = acid chloride method; Azide = azide method using pectin hydrazide). The conjugates were found useful as in the preceeding examples.

| EXAMPLE | POLYSACCHARIDE | ACTIVE COMPONENT | METHOD |
|---------|----------------|------------------|--------|
| 11. | Alginic Acid | Timothy pollen extract | N.H.P. |
| 12. | " | " | M.A. |
| 13. | " | " | W.S.D. |
| 14. | " | " | $SO_3$ |
| 15. | Pectic Acid | " | M.A. |
| 16. | " | " | W.S.D. |
| 17. | Pectin | " | Azide |
| 18. | Celluronic Acid | " | M.A. |
| 19. | " | " | W.S.D. |

-continued

| EXAMPLE | POLYSACCHARIDE | ACTIVE COMPONENT | METHOD |
|---|---|---|---|
| 20. | Carrageenan | " | W.S.D. |
| 21. | Alginic Acid | Cocksfoot pollen extract | M.A. |
| 22. | " | " | $SO_3$ |
| 23. | Alginic Acid | " | M.A. |
| 24. | " | " | $SO_3$ |
| 25. | Alginic Acid | Cocksfoot pollen extract | M.A. |
| 26. | " | " | $SO_3$ |
| 27. | Pectic Acid | " | $SO_3$ |
| 28. | " | " | $SO_3$ |
| 29. | " | " | $SO_3$ |
| 30. | " | Ragweed pollen extract | $SO_3$ |
| 31. | Alginic Acid | Birch pollen extract | M.A. |
| 32. | Alginic Acid | Horse dander extract | M.A. |
| 33. | " | Cat epithelial extract | M.A. |
| 34. | Alginic Acid | Ovalbumin | N.H.P. |
| 35. | " | " | M.A. |
| 36. | " | " | W.S.D. |
| 37. | " | " | $SO_3$ |
| 38. | " | " | A.Chl |
| 39. | Pectic Acid | " | M.A. |
| 40. | " | " | W.S.D. |
| 41. | " | " | $SO_3$ |
| 42. | Pectin | " | Azide |
| 43. | Celluronic Acid | " | W.S.D. |
| 44. | Carrageenan | " | M.A. |
| 45. | " | " | W.S.D. |
| 46. | Lichenin Uronic Acid | " | W.S.D. |
| 47. | Alginic Acid | Lactalbumin | M.A. |
| 48. | " | " | $SO_3$ |
| 49. | Alginic Acid | Haddock extract | M.A. |
| 50. | Alginic Acid | Dry rot extract | M.A. |
| 51. | Alginic Acid | Baker's yeast extract | $SO_3$ |
| 52. | Alginic Acid | Naja naja venom | $SO_3$ |
| 53. | " | Bee venom | $SO_3$ |
| 54. | Alginic Acid | Insulin | W.S.D. |
| 55. | Alginic Acid | Tetanus toxoid | $SO_3$ |
| 56. | " | Diphtheria Toxin | M.A. |
| 57. | Alginic Acid | Trypsin | M.A. |
| 58. | Pectin | " | Azide |
| 59. | Alginic Acid | Chymotrypsin | M.A. |
| 60. | Pectin | " | Azide |
| 61. | Alginic Acid | Ficin | M.A. |

What is claimed is:

1. An immunologically active conjugate capable of forming soluble sodium salts and insoluble calcium salts comprising:
    an acid polysaccharide selected from the group consisting of pectin, pectic acid, alginic acid, celluronic acid, lichenin uronic acid, and carrageenan and comprising from about 93 to 98% of said conjugate, which polysaccharide is bonded covalently by a linkage selected from the group consisting of amide, ester, and a combination of amide and ester bonds to
    an immunologically active proteinaceous component selected from the group consisting of ovalbumin, lactalbumin, insulin, trypsin, chymotrypsin, ficin, Timothy pollen extract, cocksfoot pollen extract, ragweed pollen extract, birch pollen extract, horse dander extract, cat epithelium extract, haddock extract, dry rot extract, baker's yeast extract, tetanus toxoid, diptheria toxin, bee venom, and snake venom and comprising from about 2 to 7% of said conjugate.

2. A conjugate as recited in claim 1 wherein said acid polysaccharide is alginic acid and said active component is ovalbumin.

3. A conjugate is recited in claim 1 wherein said acid polysaccharide is alginic acid and said active component is Timothy pollen extract.

4. A conjugate as recited in claim 1 wherein said acid polysaccharide is alginic acid and said active component is cocksfoot pollen extract.

5. A conjugate as recited in claim 1 wherein said acid polysaccharide is alginic acid and said active component is birch pollen extract.

6. A conjugate as recited in claim 1 wherein said acid polysaccharide is alginic acid and said active component is horse dander extract.

7. A conjugate as recited in claim 1 wherein said acid polysaccharide is alginic acid and said active component is cat opithelial extract.

8. A conjugate as recited in claim 1 wherein said acid polysaccharide is alginic acid and said active component is haddock extract.

9. A conjugate as recited in claim 1 wherein said acid polysaccharide is alginic acid and said active component is dry rot extract.

10. A conjugate as recited in claim 1 wherein said acid polysaccharide is alginic acid and said active component is baker's yeast extract.

11. A conjugate as recited in claim 1 wherein said acid polysaccharide is alginic acid and said active component is snake venom.

12. A conjugate as recited in claim 1 wherein said acid polysaccharide is alginic acid and said active component is bee venom.

13. A conjugate as recited in claim 1 wherein said acid polysaccharide is alginic acid and said active component is diptheria toxin.

14. A conjugate as recited in claim 1 wherein said acid polysaccharide is alginic acid and said active component is tetanus toxoid.

15. A conjugate as recited in claim 1 wherein said acid polysaccharide is alginic acid and said active component is lactalbumin.

16. A conjugate as recited in claim 1 wherein said acid polysaccharide is alginic acid and said active component is insulin.

17. A conjugate as recited in claim 1 wherein said acid polysaccharide is alginic acid and said active component is trypsin.

18. A conjugate as recited in claim 1 wherein said acid polysaccharide is alginic acid and said active component is chymotrypsin.

19. A conjugate as recited in claim 1 wherein said acid polysaccharide is alginic acid and said active component is ficin.

20. A conjugate as recited in claim 1 wherein said acid polysaccharide is pectic acid and said active component is ovalbumin.

21. A conjugate as recited in claim 1 wherein said acid polysaccharide is pectic acid and said active component is ragweed pollen extract.

22. A conjugate as recited in claim 1 wherein said acid polysaccharide is pectic acid and said active component is Timothy pollen extract.

23. A conjugate as recited in claim 1 wherein said acid polysaccharide is pectic acid and said active component is cocksfoot pollen extract.

24. A conjugate as recited in claim 1 wherein said acid polysaccharide is pectin and said active component is Timothy pollen extract.

25. A conjugate as recited in claim 1 wherein said acid polysaccharide is pectin and said active component is ovalbumin.

26. A conjugate as recited in claim 1 wherein said acid polysaccharide is pectin and said active component is chymotrypsin.

27. A conjugate as recited in claim 1 wherein said acid polysaccharide is pectin and said active component is trypsin.

28. A conjugate as recited in claim 1 wherein said acid polysaccharide is celluronic acid and said active component is ovalbumin.

29. A conjugate as recited in claim 1 wherein said acid polysaccharide is celluronic acid and said active component is Timothy pollen extract.

30. A conjugate as recited in claim 1 wherein said acid polysaccharide is carrageenan and said active component is ovalbumin.

31. A conjugate as recited in claim 1 wherein said acid polysaccharide is carrageenan and said active component is Timothy pollen extract.

32. A conjugate as recited in claim 1 wherein said acid polysaccharide is lichenin uronic acid and said active component is ovalbumin.

* * * * *